United States Patent
Williams et al.

(10) Patent No.: US 7,163,554 B2
(45) Date of Patent: *Jan. 16, 2007

(54) ENDOPROSTHESES AND METHODS OF MANUFACTURE

(75) Inventors: Michael S. Williams, Santa Rosa, CA (US); Richard A. Glenn, Santa Rosa, CA (US); Jeffrey A. Smith, Santa Rosa, CA (US); Kevin D. Holbrook, Windsor, CA (US); Joseph M. DeSimone, Chapel Hill, NC (US)

(73) Assignee: SyneCor, LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/984,112

(22) Filed: Nov. 8, 2004

(65) Prior Publication Data

US 2005/0152938 A1   Jul. 14, 2005

Related U.S. Application Data

(63) Continuation-in-part of application No. 10/342,622, filed on Jan. 15, 2003, now Pat. No. 6,887,266.

(60) Provisional application No. 60/546,905, filed on Feb. 23, 2004, provisional application No. 60/426,737, filed on Nov. 15, 2002, provisional application No. 60/426,734, filed on Nov. 15, 2002.

(51) Int. Cl.
  *A61F 2/06*   (2006.01)

(52) U.S. Cl. ................................. 623/1.22; 623/1.16
(58) Field of Classification Search ............... 623/1.22, 623/1.16
See application file for complete search history.

(56) References Cited

U.S. PATENT DOCUMENTS

| | | | | | |
|---|---|---|---|---|---|
| 5,061,275 | A | * | 10/1991 | Wallsten et al. | 623/1.22 |
| 5,741,293 | A | * | 4/1998 | Wijay | 623/1.15 |
| 5,876,419 | A | * | 3/1999 | Carpenter et al. | 623/1.16 |
| 5,938,695 | A | * | 8/1999 | Borghi | 623/1.16 |
| 6,887,266 | B1 | * | 5/2005 | Williams et al. | 623/1.16 |
| 2001/0003801 | A1 | * | 6/2001 | Strecker | 623/1.11 |

* cited by examiner

*Primary Examiner*—Eduardo C. Robert
*Assistant Examiner*—Thomas J. Sweet
(74) *Attorney, Agent, or Firm*—Deanna J. Shirley

(57) ABSTRACT

A woven tubular endoprosthesis comprising means for locking the endoprosthesis in a deployed configuration is disclosed. The means for locking the endoprosthesis may comprise locking protrusions, notches, a chemical bond, a curable bond, or other mechanism. The woven fibers comprising the endoprosthesis may be hollow and comprise circumferentially oriented polymeric chains, and may be filled with a curable material. A method of treatment using an endoprosthesis according to the invention is also disclosed.

11 Claims, 16 Drawing Sheets

ENDOPROSTHESES AND METHODS OF MANUFACTURE

RELATED APPLICATIONS

This application is a continuation in part of U.S. patent application Ser. No. 10/342,622, filed Jan. 15, 2003 now U.S. Pat. No. 6,887,266, and claims the benefit of Provisional U.S. Patent Application Ser. No. 60/426,737, filed Nov. 15, 2002, Provisional U.S. Patent Application Ser. No. 60/426,734 filed Nov. 15, 2002, U.S. patent application Ser. No. 10/342,771, filed Jan. 15, 2003, and Provisional U.S. Patent Application Ser. No. 60/546,905, filed Feb. 23, 2004 the disclosures of which are hereby incorporated by reference, each in its entirety.

FIELD OF THE INVENTION

The invention herein relates generally to medical devices and the manufacture thereof, and more particularly to improved endoprostheses for use in the treatment of strictures in lumens of the body.

BACKGROUND OF THE INVENTION

Ischemic heart disease is the major cause of death in industrialized countries. Ischemic heart disease, which often results in myocardial infarction, is a consequence of coronary atherosclerosis. Atherosclerosis is a complex chronic inflammatory disease and involves focal accumulation of lipids and inflammatory cells, smooth muscle cell proliferation and migration, and the synthesis of extracellular matrix. *Nature* 1993; 362:801–809. These complex cellular processes result in the formation of atheromatous plaque, which consists of a lipid-rich core covered with a collagen-rich fibrous cap, varying widely in thickness. Further, plaque disruption is associated with varying degrees of internal hemorrhage and luminal thrombosis because the lipid core and exposed collagen are thrombogenic. *J Am Coll Cardiol.* 1994; 23:1562–1569 Acute coronary syndrome usually occurs as a consequence of such disruption or ulceration of a so called "vulnerable plaque". *Arterioscler Thromb Vasc Biol.* Volume 22, No. 6, June 2002, p. 1002.

In addition to coronary bypass surgery, a current treatment strategy to alleviate vascular occlusion includes percutaneous transluminal coronary angioplasty, expanding the internal lumen of the coronary artery with a balloon. Roughly 800,000 angioplasty procedures are performed in the U.S. each year (*Arteriosclerosis, Thrombosis, and Vascular Biology* Volume 22, No. 6, June 2002, p. 884). However, 30% to 50% of angioplasty patients soon develop significant restenosis, a narrowing of the artery through migration and growth of smooth muscle cells.

In response to the significant restenosis rate following angioplasty, percutaneously placed endoprostheses have been extensively developed to maintain fluid flow through a diseased coronary artery. Such endoprostheses, or stents, which have been traditionally fabricated using metal alloys, include self-expanding or balloon-expanded devices that are "tracked" through the vasculature and deployed proximate one or more lesions. Stents considerably enhance the long-term benefits of angioplasty, but 10% to 50% of patients receiving stents still develop restenosis. (*J Am Coll Cardiol.* 2002; 39:183–193. Consequently, a significant portion of the relevant patient population undergoes continued monitoring and, in many cases, additional treatment.

Continued improvements in stent technology aim at producing easily tracked, easily visualized and readily deployed stents, which exhibit the requisite radial strength without sacrificing a small delivery profile and sufficient flexibility to traverse the diseased human vasculature. Further, numerous therapies directed to the cellular mechanisms of accumulation of inflammatory cells, smooth muscle cell proliferation and migration show tremendous promise for the successful long-term treatment of ischemic heart disease. Consequently, advances in coupling delivery of such therapies to the mechanical support of vascular endoprostheses, delivered proximate the site of disease, offer great hope to the numerous individuals suffering heart disease.

While advances in the understanding of ischemic heart disease as a complex chronic inflammatory process take place, traditional diagnostic techniques such as coronary angiography yield to next generation imaging modalities. In fact, coronary angiography may not be at all useful in identifying inflamed atherosclerotic plaques that are prone to producing clinical events. Imaging based upon temperature differences, for example, are undergoing examination for use in detecting coronary disease. Magnetic resonance imaging (MRI) is currently emerging as the state of the art diagnostic arterial imaging, enhancing the detection, diagnosis and monitoring of the formation of vulnerable plaques. Transluminal intervention guided by MRI is expected to follow. However, metals produce distortion and artifacts in MR images, rendering use of the traditionally metallic stents in coronary, biliary, esophageal, ureteral, and other body lumens incompatible with the use of MRI.

Consequently, an emerging clinical need for interventional devices that are compatible with and complementary to new imaging modalities is evident. Further, devices that exhibit improved trackability to previously undetectable disease within remote regions of the body, especially the coronary vasculature are needed. And finally, devices that both exhibit improved mechanical support and are readily compatible with adjunct therapies in order to lower or eliminate the incidence of restenosis are needed.

SUMMARY OF THE INVENTION

An endoprosthesis is disclosed comprising a length, one or more fibers and an axis extending generally along said length, said one or more fibers comprising a braid comprising one or more points of intersection, said endoprosthesis further defining a generally tubular structure, a delivery configuration and a deployed configuration, said one or more fibers comprising one or more locking elements proximate said one or more points of intersection, wherein upon deployment, one or more of said fibers engages itself or another fiber proximate one or more of said points of intersection via said locking elements to maintain said endoprosthesis in said deployed configuration, and where said endoprosthesis does not comprise a primarily axially oriented element or fiber. An endoprosthesis according to the invention may comprise one or more erodible materials. The locking elements may comprise locking protrusions, one or more notches, or male and female elements. One or more fibers may comprise a chemical bond at said one or more points of intersection when said endoprosthesis is in said deployed configuration, or one or more thermocoupling element. An endoprosthesis according to the invention may comprise one or more curable materials.

An endoprosthesis according to the invention may comprise a length, one or more fibers, an axis extending generally along said length, said one or more fibers oriented substantially in a first direction and one or more fibers oriented substantially in a second direction to form one or more points of intersection and a woven tubular structure also comprising a delivery configuration and a deployed configuration, said one or more fibers comprising one or more locking elements proximate said one or more points of intersection, wherein upon deployment, one or more of said fibers engages itself or another fiber proximate one or more of said points of intersection via said locking elements to maintain said endoprosthesis in said deployed configuration, and where said endoprosthesis does not comprise a fiber oriented in substantially a third direction. One or more of said fibers may be hollow and filled with a curable material, and may comprise polymers chains in substantially circumferential orientation.

A method of treatment of a stenosis of a body lumen is disclosed comprising the steps of providing a generally tubular endoprosthesis comprising a delivery configuration and a deployed configuration and formed from one or more fibers comprising calcium and one or more fibers comprising alginate, wherein said fibers comprise an erodible coating and one or more points of intersection; placing said endoprosthesis in a body lumen; deploying said endoprosthesis; allowing said erodible coating to erode, thereby exposing one or more calcium fiber to one or more alginate fiber; and allowing said one or more calcium fiber to bond to one or more alginate fiber at one or more points of intersection.

A method of treatment of a stenosis of a body lumen is disclosed comprising the steps of providing a generally tubular endoprosthesis comprising a delivery configuration and a deployed configuration formed from one or more hollow fibers filled with one or more curable materials; placing said endoprosthesis in a body lumen; deploying said endoprosthesis; and allowing said curable material to cure. If one or more of said curable materials is photocurable, an additional step of exposing said endoprosthesis to light in order to cure said material may be taken.

DETAILED DESCRIPTION OF THE INVENTION

Figure 1:
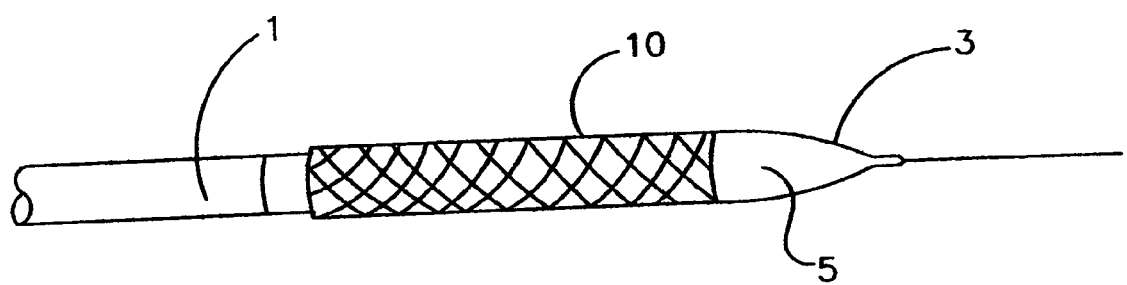
FIG. 1 is a plan view of the distal end of a conventional balloon catheter having a stent according to the invention mounted thereon.

Although the invention herein is not limited as such, some embodiments of the invention comprise materials that are erodible. "Erodible" refers to the ability of a material to maintain its structural integrity for a desired period of time, and thereafter gradually undergo any of numerous processes whereby the material substantially loses tensile strength and mass. Examples of such processes comprise hydrolysis, enzymatic and non-enzymatic degradation, oxidation, enzymatically-assisted oxidation, and others, thus including bioresorption, dissolution, and mechanical degradation upon interaction with a physiological environment into components that the patient's tissue can absorb, metabolize, respire, and/or excrete. Polymer chains are cleaved by hydrolysis and are eliminated from the body through the Krebs cycle, primarily as carbon dioxide and in urine. "Erodible" and "degradable" are intended to be used interchangeably herein.

A "self-expanding" endoprosthesis has the ability to revert readily from a reduced profile configuration to a larger profile configuration in the absence of a restraint upon the device that maintains the device in the reduced profile configuration.

"Balloon expandable" refers to a device that comprises a reduced profile configuration and an expanded profile configuration, and undergoes a transition from the reduced configuration to the expanded configuration via the outward radial force of a balloon expanded by any suitable inflation medium.

The term "balloon assisted" refers to a self-expanding device the final deployment of which is facilitated by an expanded balloon.

The term "fiber" refers to any generally elongate member fabricated from any suitable material, whether polymeric, metal or metal alloy, natural or synthetic. A fiber may be solid, hollow, or initially hollow and later filled with a material during the fabrication of the fiber.

The phrase "points of intersection", when used in relation to fiber(s), refers to any point at which a portion of a fiber or two or more fibers cross, overlap, wrap, pass tangentially, pass through one another, or come near to or in actual contact with one another.

As used herein, a device is "implanted" if it is placed within the body to remain for any length of time following the conclusion of the procedure to place the device within the body.

As used herein, the term "braid" refers to any braid or mesh or similar woven structure produced from between 1 and several hundred longitudinal and/or transverse elongate elements woven, braided, knitted, helically wound, or intertwined any manner, at angles between 0 and 180 degrees and usually between 45 and 105 degrees, depending upon the overall geometry and dimensions desired.

Unless specified, suitable means of attachment may include by thermal melt bond, chemical bond, adhesive, sintering, welding, or any means known in the art.

"Shape memory" refers to the ability of a material to undergo structural phase transformation such that the material may define a first configuration under particular physical and/or chemical conditions, and to revert to an alternate configuration upon a change in those conditions. Shape memory materials may be metal alloys including but not limited to nickel titanium, or may be polymeric. A polymer is a shape memory polymer if the original shape of the polymer is recovered by heating it above a shape recovering temperature (defined as the transition temperature of a soft segment) even if the original molded shape of the polymer is destroyed mechanically at a lower temperature than the shape recovering temperature, or if the memorized shape is recoverable by application of another stimulus. Such other stimulus may include but is not limited to pH, salinity, hydration, and others. Some embodiments according to the invention may comprise one or more polymers having a structure that assumes a first configuration, a second configuration, and a hydrophilic polymer of sufficient rigidity coated upon at least a portion of the structure when the device is in the second configuration. Upon placement of the device in an aqueous environment and consequent hydration of the hydrophilic polymer, the polymer structure reverts to the first configuration.

As used herein, the term "segment" refers to a block or sequence of polymer forming part of the shape memory polymer. The terms hard segment and soft segment are relative terms, relating to the transition temperature of the segments. Generally speaking, hard segments have a higher glass transition temperature than soft segments, but there are exceptions. Natural polymer segments or polymers include but are not limited to proteins such as casein, gelatin, gluten, zein, modified zein, serum albumin, and collagen, and polysaccharides such as alginate, chitin, celluloses, dextrans, pullulane, and polyhyaluronic acid; poly(3-hydroxyalkanoate)s, especially poly(.beta.-hydroxybutyrate), poly (3-hydroxyoctanoate) and poly(3-hydroxyfatty acids).

Representative natural erodible polymer segments or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers.

Suitable synthetic polymer blocks include polyphosphazenes, poly(vinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof.

Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly (octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, arboxymethyl cellulose, cellulose triacetate and cellulose sulfate sodium salt. These are collectively referred to herein as "celluloses".

Examples of synthetic degradable polymer segments or polymers include polyhydroxy acids, such as polylactides, polyglycolides and copolymers thereof; poly(ethylene terephthalate); poly(hydroxybutyric acid); poly(hydroxyvaleric acid); poly[lactide-co-(.epsilon.-caprolactone)]; poly [glycolide-co-(.epsilon.-caprolactone)]; polycarbonates, poly(pseudo amino acids); poly(amino acids); poly(hydroxyalkanoate)s; polyanhydrides; polyortho esters; and blends and copolymers thereof.

For those embodiments comprising a shape memory polymer, the degree of crystallinity of the polymer or polymeric block(s) is between 3 and 80%, more often between 3 and 65%. The tensile modulus of the polymers below the transition temperature is typically between 50 MPa and 2 GPa (gigapascals), whereas the tensile modulus of the polymers above the transition temperature is typically between 1 and 500 MPa. Most often, the ratio of elastic modulus above and below the transition temperature is 20 or more.

The melting point and glass transition temperature of the hard segment are generally at least 10 degrees C., and preferably 20 degrees C., higher than the transition temperature of the soft segment. The transition temperature of the hard segment is preferably between—60 and 270 degrees C., and more often between 30 and 150 degrees C. The ratio by weight of the hard segment to soft segments is between about 5:95 and 95:5, and most often between 20:80 and 80:20. The shape memory polymers contain at least one physical crosslink (physical interaction of the hard segment) or contain covalent crosslinks instead of a hard segment. The shape memory polymers can also be interpenetrating networks or semi-interpenetrating networks.

Rapidly erodible polymers such as poly(lactide-co-glycolide)s, polyanhydrides, and polyorthoesters, which have carboxylic groups exposed on the external surface as the smooth surface of the polymer erodes, can also be used. In addition, polymers containing labile bonds, such as polyanhydrides and polyesters, are well known for their hydrolytic reactivity. Their hydrolytic degradation rates can generally be altered by simple changes in the polymer backbone and their sequence structure.

Examples of suitable hydrophilic polymers include but are not limited to poly(ethylene oxide), polyvinyl pyrrolidone, polyvinyl alcohol, poly(ethylene glycol), polyacrylamide poly(hydroxy alkyl methacrylates), poly(hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof.

Hydrogels can be formed from polyethylene glycol, polyethylene oxide, polyvinyl alcohol, polyvinyl pyrrolidone, polyacrylates, poly (ethylene terephthalate), poly(vinyl acetate), and copolymers and blends thereof. Several polymeric segments, for example, acrylic acid, are elastomeric only when the polymer is hydrated and hydrogels are formed. Other polymeric segments, for example, methacrylic acid, are crystalline and capable of melting even when the polymers are not hydrated. Either type of polymeric block can be used, depending on the desired application and conditions of use.

Curable materials include any material capable of being able to transform from a fluent or soft material to a harder material, by cross-linking, polymerization, or other suitable process. Materials may be cured over time, thermally, chemically, or by exposure to radiation. For those materials that are cured by exposure to radiation, many types of radiation may be used, depending upon the material. Wavelengths in the spectral range of about 100–1300 nm may be used. The material should absorb light within a wavelength range that is not readily absorbed by tissue, blood elements, physiological fluids, or water. Ultraviolet radiation having a wavelength ranging from about 100–400 nm may be used, as well as visible, infrared and thermal radiation. The following materials are examples of curable materials: urethanes, polyurethane oligomer mixtures, acrylate monomers, aliphatic urethane acrylate oligomers, acrylamides, UV curable epoxies, photopolymerized polyanhydrides and other UV curable monomers and polymers. Alternatively, the curable material can be a material capable of being chemically cured, such as silicone based compounds which undergo room temperature vulcanization.

Some embodiments according to the invention comprise materials that are cured in a desired pattern. Such materials may be cured by any of the foregoing means. Further, for those materials that are photocurable, such a pattern may be created by coating the material in a negative image of the desired pattern with a masking material using standard photoresist technology. Absorption of both direct and incident radiation is thereby prevented in the masked regions, curing the device in the desired pattern. A variety of biocompatibly eroding coating materials may be used for such "masking", including but not limited to gold, magnesium, aluminum, silver, copper, platinum, inconel, chrome, titanium indium, indium tin oxide. Projection optical photolithography systems that utilize the vacuum ultraviolet wavelengths of light below 240 nm provide benefits in terms of achieving smaller feature dimensions. Such systems that utilize ultraviolet wavelengths in the 193 nm region or 157 nm wavelength region have the potential of improving precision masking devices having smaller feature sizes.

Though not limited thereto, some embodiments according to the invention have been surface treated to comprise one or more therapeutic substances that will elute from the structure of prosthesis independently or as the material comprising the stent erodes. Alternatively, therapeutic substances may be incorporated into the materials that comprise the endoprosthesis. According to the invention, such surface treatment and/or incorporation of therapeutic substances may be performed utilizing one or more of numerous processes that utilize carbon dioxide fluid, e.g., carbon dioxide in a liquid or supercritical state.

A supercritical fluid is a substance above its critical temperature and critical pressure (or "critical point"). Compressing a gas normally causes a phase separation and the appearance of a separate liquid phase. However, all gases have a critical temperature above which the gas cannot be liquefied by increasing pressure, and a critical pressure or pressure which is necessary to liquefy the gas at the critical temperature. For example, carbon dioxide in its supercritical state exists as a form of matter in which its liquid and gaseous states are indistinguishable from one another. For carbon dioxide, the critical temperature is about 31 degrees C. (88 degrees D) and the critical pressure is about 73 atmospheres or about 1070 psi.

The term "supercritical carbon dioxide" as used herein refers to carbon dioxide at a temperature greater than about 31 degrees C. and a pressure greater than about 1070 psi. Liquid carbon dioxide may be obtained at temperatures of from about −15 degrees C. to about −55 degrees C. and pressures of from about 77 psi to about 335 psi. One or more solvents and blends thereof may optionally be included in the carbon dioxide. Illustrative solvents include, but are not limited to, tetraflouroisopropanol, chloroform, tetrahydrofuran, cyclohexane, and methylene chloride. Such solvents are typically included in an amount, by weight, of up to about 20%.

In general, carbon dioxide may be used to effectively lower the glass transition temperature of a polymeric material to facilitate the infusion of pharmacological agent(s) into the polymeric material. Such agents include but are not limited to hydrophobic agents, hydrophilic agents and agents in particulate form. For example, following fabrication, an endoprosthesis and a hydrophobic pharmacological agent may be immersed in supercritical carbon dioxide. The supercritical carbon dioxide "plasticizes" the polymeric material, that is, it allows the polymeric material to soften at a lower temperature, and facilitates the infusion of the pharmacological agent into the polymeric endoprosthesis or polymeric coating of a stent at a temperature that is less likely to alter and/or damage the pharmacological agent.

As an additional example, an endoprosthesis and a hydrophilic pharmacological agent can be immersed in water with an overlying carbon dioxide "blanket". The hydrophilic pharmacological agent enters solution in the water, and the carbon dioxide "plasticizes" the polymeric material, as described above, and thereby facilitates the infusion of the pharmacological agent into a polymeric endoprosthesis or a polymeric coating of an endoprosthesis.

As yet another example, carbon dioxide may be used to "tackify", or render more adherent a polymeric endoprosthesis or a polymeric coating on an endoprosthesis to facilitate the application of a pharmacological agent thereto in a dry, micronized form. A membrane-forming polymer, selected for its ability to allow the diffusion of the pharmacological agent therethrough, may then be applied in a layer over the endoprosthesis. Following curing by suitable means, a membrane that permits diffusion of the pharmacological agent over a predetermined time period forms.

In alternative embodiments of the present invention, at least one monomer or comonomer can be solubilized in carbon dioxide and copolymerized with a fluoromonomer. Any suitable monomers or comonomers can be employed, including, but not limited to, acrylate, methacrylate, acrylamide, methacrylamide, styrenics, ethylene, and vinyl ether monomers. The copolymerizations of the present invention may be carried out under temperature and pressure conditions similar to those given above.

Objectives of therapeutics substances incorporated into materials forming or coating an endoprosthesis according to the invention include reducing the adhesion and aggregation of platelets at the site of arterial injury, block the expression of growth factors and their receptors; develop competitive antagonists of growth factors, interfere with the receptor signaling in the responsive cell, promote an inhibitor of smooth muscle proliferation. Anitplatelets, anticoagulants, antineoplastics, antifibrins, enzymes and enzyme inhibitors, antimitotics, antimetabolites, anti-inflammatories, antithrombins, antiproliferatives, antibiotics, and others may be suitable.

As an example, 100% high molecular weight PLLA is a highly crystalline material that retains the elastic modulus required of a polymeric erodible stent. However, the material in its natural state is too brittle to expand from a rolled down diameter to diameters in the vascular tract. According to the invention, the material may be heated to a temperature above its melting temperature (200° C.–210° C.) for 20–45 seconds (the amount of time and exact temperature are design dependent) and cooled rapidly to quench the material. The foregoing process decreases the percentage of crystallinity, yet has very little effect on the elastic modulus of the material. Further, the percentage elongation may be increased by as much as a factor of 60 (from approximately 5% to as high as 300%).

Further, the annealing process (comprising heating the materials according to chosen parameters including time and temperature) increases polymer chain crystallization, thereby increasing the strength of the material. If a more resilient material is added to PLLA in order to increase the % elongation to failure, the resulting material may have a low elastic modulus. Annealing the material will increase the percentage of crystallinity and increase the elastic modulus. By heating the material to a temperature within its cold crystallization temperature (approximately 100° C.–110° C., see FIG. 5) for a period of time that is design and process dependent (10–15 min., for example), the material will have properties that yield acceptable in vitro results. An additional process by which to increase the modulus of elasticity comprises adding biocompatible fillers that may be organic or inorganic, and may include metals. Examples of inorganic fillers include but are not limited to calcium carbonate, sodium chloride, magnesium salts, and others.

An endoprosthesis such as a stent or an anchor according to the invention may be manufactured according to steps comprising forming hollow fiber, or small tube from the selected polymers processed as above via an extrusion process and subjecting the tube to gas and pressure within a mold. The step of subjecting the tube to gas and pressure increases the diameter of the tube to a selected diameter and simultaneously aligns the polymeric chains circumferentially. The resulting circumferential orientation of the polymer chains confers increased radial strength upon hollow fiber. In addition, the resulting circumferential alignment confers added axial flexibility. The enhanced hollow fiber may then be filled with a curable material and woven into a finished device. The curable material may be cured before or after delivering the device to the treatment site.

Details of the invention can be better understood from the following descriptions of specific embodiments according to the invention. As an example, in FIG. 1, distal end 3 of standard delivery catheter 1 is shown, bearing endoprosthesis 10. Although an endoprosthesis according to the invention may be self-expanding, endoprosthesis 10 mounted on distal end 3 is balloon-expandable. Accordingly, endoprosthesis 10 is deployed via delivery catheter 1, which comprises balloon 5 at distal end 3. Endoprosthesis 10, which may be fabricated from any of the foregoing conventional or shape memory materials including metal alloys, polymers, or other suitable materials selected for molecular weight, chemical composition and other properties, manufactured to achieve any desired geometries and processed according to any of the foregoing descriptions, is "crimped" down upon balloon 5 into its low-profile delivery configuration. Endoprosthesis 10 can then be tracked to a lesion site within a lumen of the body where endoprosthesis 10 can be deployed. In order to deploy endoprosthesis 10, balloon 5 is inflated via inflation medium through catheter 1. The outward radial force of expanding balloon 5 expands endoprosthesis 10 to its deployed configuration.

Figure 2:
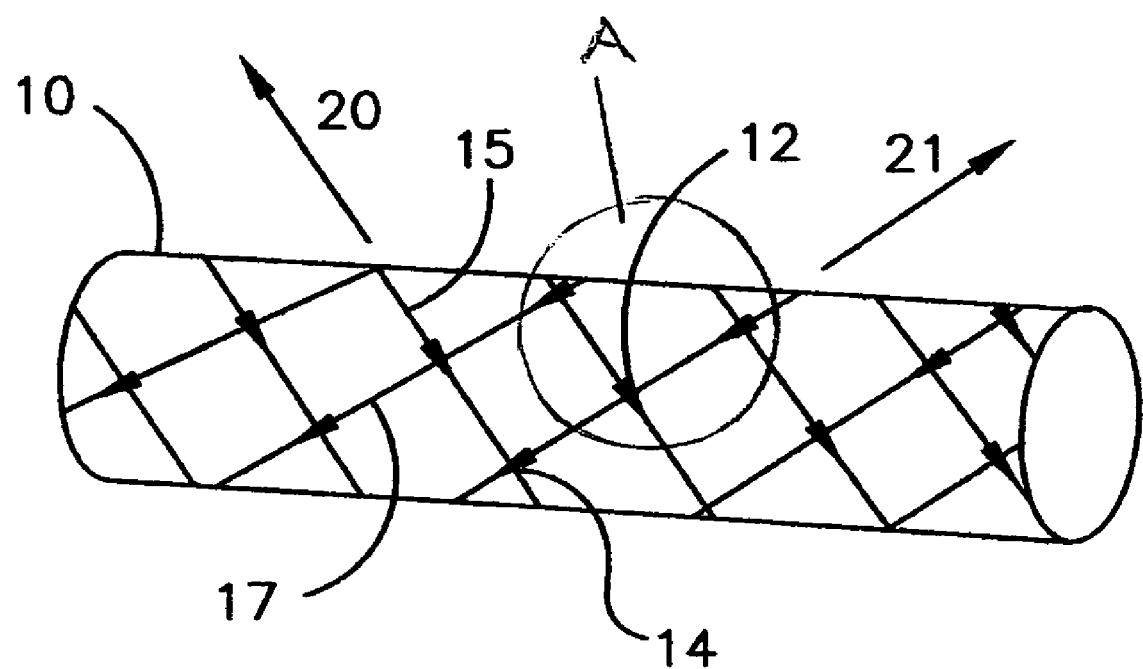
FIG. 2 shows the embodiment of FIG. 1 in its deployed configuration.

FIG. 2 illustrates endoprosthesis 10 in its deployed configuration, following removal of catheter 1. Accordingly, endoprosthesis 10 is at its deployed diameter, which may be between 0.5 mm and 4.0 mm, depending upon the size of the vessel of the patient (not pictured). Endoprosthesis 10 comprises between one and fifty fibers 15 and 17, which may be homogenous or composite, fabricated from one or more different materials. Further, fibers 15 and 17 may be solid or hollow, or initially hollow and later filled with, for example, a curable material (not pictured). If hollow, tubular fibers may be prepared via an extrusion process and then, prior to filling, subjecting the tube to gas and pressure within a mold. The step of subjecting the tube to gas and pressure increases the diameter of the tubular fiber to a selected diameter and simultaneously aligns the polymeric chains circumferentially. The resulting circumferential orientation of the polymer chains confers increased radial strength upon the finished device. In addition, the resulting circumferential alignment confers added axial flexibility. The tubular fibers may additionally be subjected to an annealing process in order to further strengthen the fibers. The foregoing processes are more fully described in U.S. Provisional Patent Application Ser. No. 60/546,905 and are hereby incorporated as if set forth fully herein. If the tubular fibers are then filled with a curable material, the curable material may be allowed to cure. In the alternative, if the tubular fiber is filled with a photocurable material, for example, the endoprosthesis may be deployed and then exposed to light in order to cure the material. Examples of the foregoing processes are more fully described in U.S. Provisional Patent Application 60/426,734 and U.S. patent application Ser. No. 10/342,771, and are hereby incorporated as if set forth fully herein. Endoprosthesis 10 may alternatively comprise additional fibers. Fibers 15 and 17 are braided in any suitable manner as discussed above to intersect one another at one or more points and to form a generally tubular structure.

Locking elements 12 protrude from fibers 15 in a first direction 20 at an angle between 1 and 90 degrees, and most suitably at an angle between 10 and 45 degrees. Locking elements 12 are spaced apart from one another at a distance of between 1.0 mm and 5.0 mm, and most often at a distance of 1.0 mm and 3.0 mm, and can operate singly, in pairs, or in groups. Similarly, locking elements 14 protrude from fibers 17 in a second direction 21, perpendicular to first direction 20, and are spaced apart from one another at a distance corresponding to the desired dimensions of stent 10. Locking elements 12 are oriented such that when endoprosthesis 10 is undergoing expansion, fibers 15 pass over locking elements 12 in a first direction 20 until endoprosthesis 10 is expanded to a desired diameter. Similarly, fibers 17 pass over locking elements 14 in a second direction 21, until stent 10 is expanded to a desired diameter. Fibers 15 and 17 cannot pass over locking elements 14 and 17 in a reverse direction. Consequently, when stent 10 has reached a desired diameter, locking elements 12 and 14 engage fibers 15 and 17 respectively where fibers 15 and 17 intersect one another. Locking elements 12 and 14 thereafter prevent fibers 15 and 17 from sliding past one another, thereby maintaining the position of fibers 15 and 17 with respect to one another. Consequently, endoprosthesis 10 is prevented from returning to a smaller diameter, thereby enabling endoprosthesis 10 to exert a continual outward radial force upon the walls of the vessel or duct of a patient in order to enhance or restore the flow of fluids therethrough.

Figure 3:
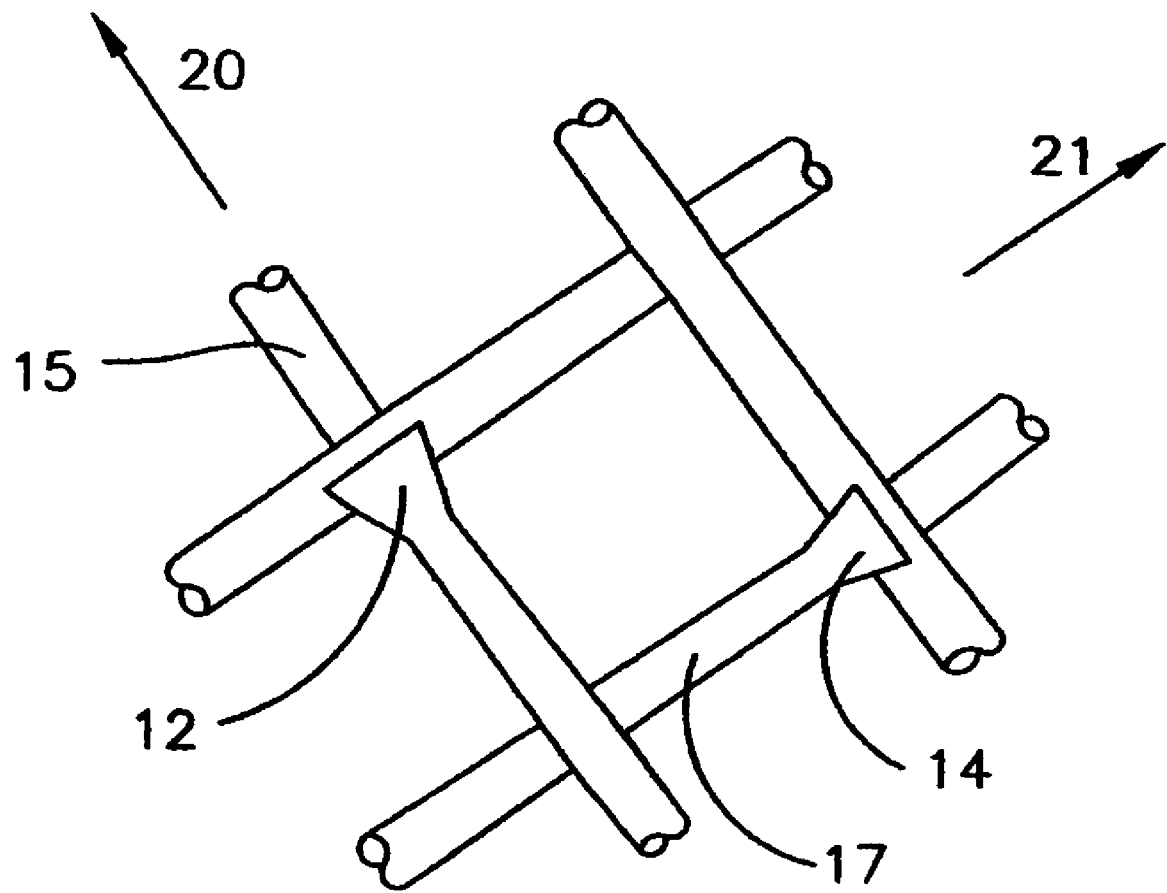
FIG. 3 illustrates detail area A of FIG. 2.

FIG. 3 depicts endoprosthesis 10 of FIG. 2 in greater detail at area A. Although alternative arrangements are possible, pairs of locking elements 12 protrude from fibers 15 in a first direction as depicted by arrow 20, engaging fibers 17 where they intersect with fibers 15 and exerting a force in direction of arrow 20. Similarly, although they may also, for example, alternatively act solely, pairs of locking elements 14 protrude from fibers 17 in a second direction 21. Locking elements 14 exert a force on fibers 17 in a second direction 21, perpendicular to direction 20, as depicted by arrow 21. The positions of fibers 15 and 17 with respect to one another are thereby maintained, and endoprosthesis 10 is able to maintain its treatment diameter and exert an outward radial force upon the walls of the narrowed vessel, in order that fluid flow through the lumen is enhanced or restored.

Figure 4A:
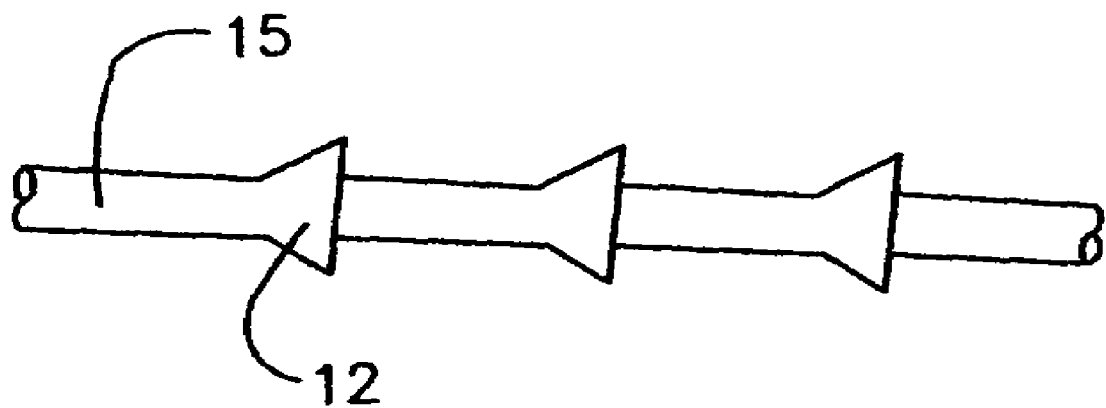
FIG. 4A shows an example of fibers that may be employed to fabricate the embodiment of FIGS. 1–3.

As shown in FIG. 4A, fiber 15 comprises one or more locking elements 12, which may be arranged solely, in pairs, or in any number of alternative suitable arrangements. Locking elements 12 may be affixed to fiber 15 in any number of suitable manners known in the art including but not limited to affixing by adhesives, welding, melt attaching, or others, or may be bump coextruded with fiber 15. Locking elements 12 may be fabricated of the same material as fiber 15, or may be chosen from a group of materials that exhibits greater rigidity than that of fiber 15. Endoprosthesis 10 may alternatively further comprise one or more therapeutic agents for elution in situ.

Figure 5:
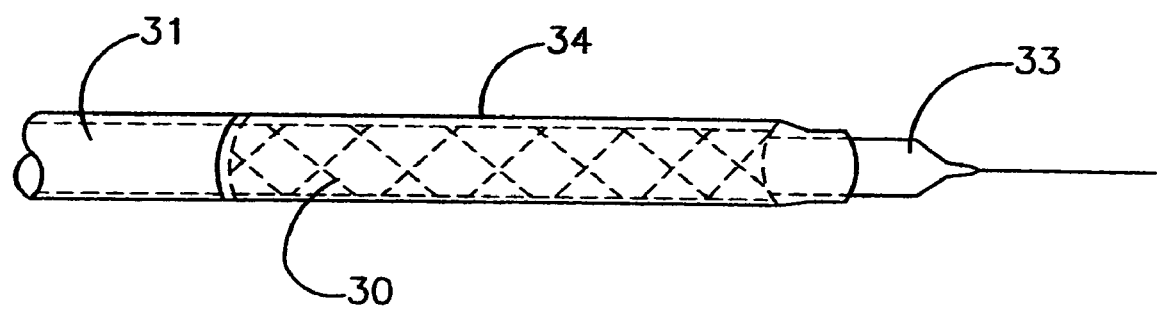
FIG. 5 is a plan view of the distal end of a conventional delivery catheter having an alternative embodiment according to the invention mounted thereon.

Turning now to FIG. 5, another embodiment according to the invention is disclosed. Distal end 33 of exemplary delivery catheter 31 is shown. Although an endoprosthesis according to the invention may in the alternative be balloon expandable, endoprosthesis 30 mounted on distal end 33 is self-expanding. Accordingly, endoprosthesis 30 is crimped down to its low-profile delivery configuration for tracking through the patient's vasculature, and maintained in the low-profile configuration via sheath 34. When distal end 33 is positioned proximate a lesion to be treated (not shown), sheath 34 is withdrawn, allowing endoprosthesis 30 to be returned to its larger diameter, deployed configuration. Endoprosthesis 30 may be fabricated from any number of suitable shape memory materials, including polymeric materials and metal alloys discussed above, chosen for desired chemical properties, molecular weight, and other characteristics, and processed to achieve sterilization, desired geometries and in vivo lifetime.

Figure 6:
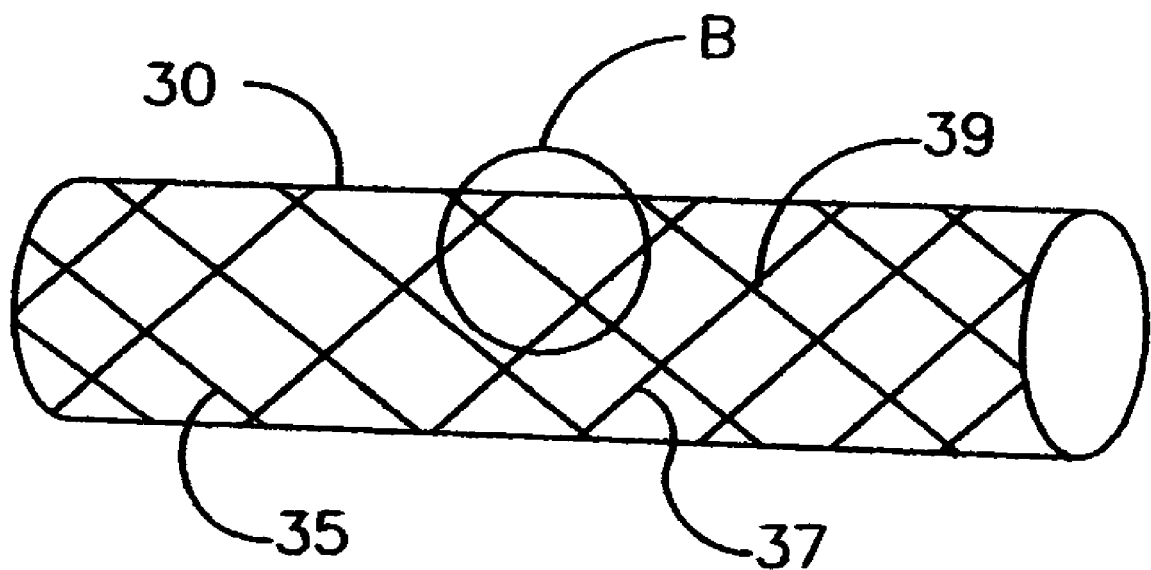
FIG. 6 shows the embodiment of FIG. 5 in its deployed configuration.

FIG. 6 depicts endoprosthesis 30 in its deployed configuration. Similar to the embodiment discussed in relation to FIGS. 1–4 above, endoprosthesis 30 is braided to form a generally tubular structure with fibers 35 and 37 intersecting at one or more points of intersection 39. Fibers 35 and 37, which may be homogenous or composite, and may be fabricated of the same or different materials, and may be solid or hollow, may comprise circumferentially oriented polymers, and, if hollow, may be filled with a curable material, intersect one another at angles of between 25 and 105 degrees. When endoprosthesis 30 has expanded to its desired deployment diameter, fibers 35 and 37 "nest" with one another at points of intersection 39, thereby locking endoprosthesis 30 in its deployed configuration. Fibers 35 and 37 are permitted to nest with one another via notches 40, which are between 0.25 mm and 1.0 mm, spaced apart from one another at a distance of between 1.0 mm and 5.0 mm, depending upon the desired deployment dimensions.

Figure 7:
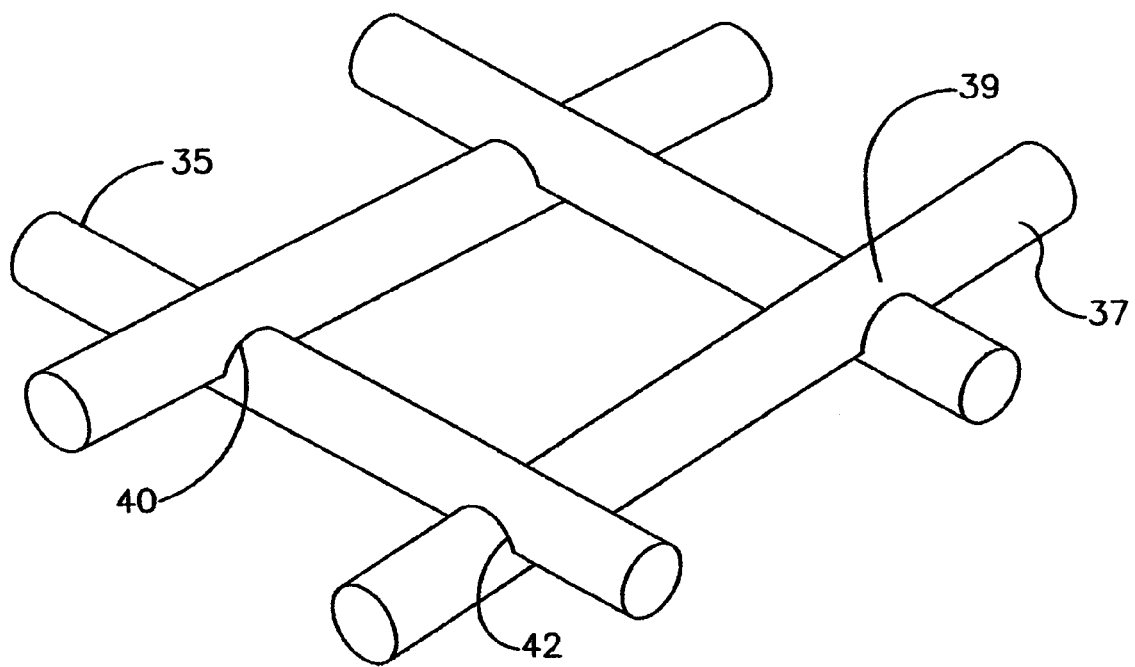
FIG. 7 illustrates detail area B of FIG. 6.
Figure 8A:
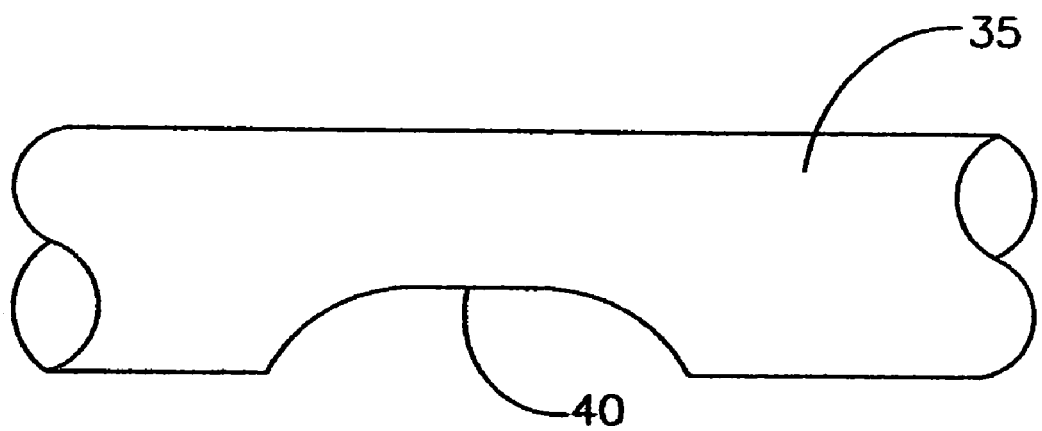
FIGS. 8A and 8B show examples of fibers that may be employed to fabricate an embodiment according to the invention.
Figure 8B:
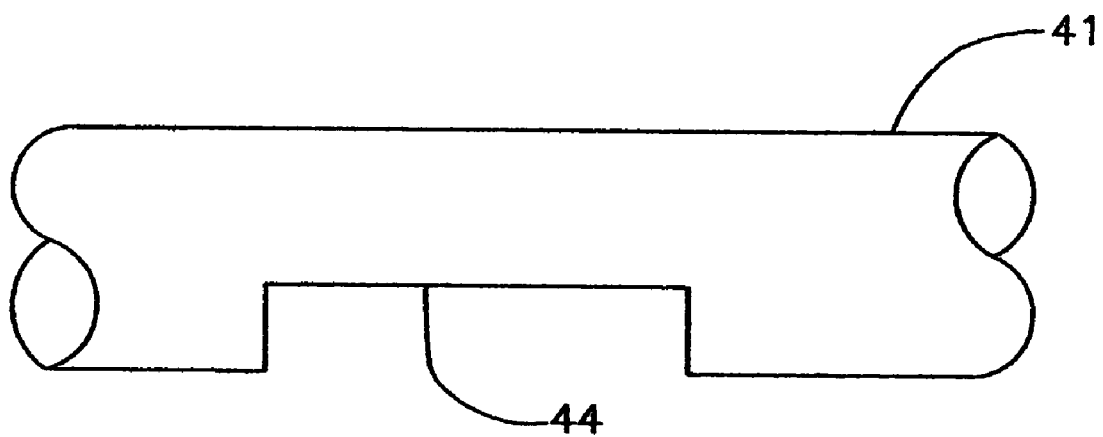

Notches 40 can be better seen in FIGS. 7 and 8. For example, FIG. 7 depicts a portion of endoprosthesis 30 in greater detail at area B, illustrating fibers 35 and 37 in their nested configuration. FIGS. 8A and 8B depict alternative examples of fibers that may be used to fabricate an endoprosthesis according to the invention. Fiber 35, shown in isolation in FIG. 8A, comprises notch 40. Similarly, fiber 41 of FIG. 8B, having an alternative configuration, comprises notches 44. Other configurations may be suitable.

When stent 30 is in its delivery configuration, notches 40 and 42 are disengaged from fibers 35 and 37. Upon deployment, as the shape memory properties of the materials used to fabricate endoprosthesis 30 cause endoprosthesis 30 to return to its deployed configuration, stent 30 exhibits an outward radial force. Further, fibers 35 and 37 spring to "nest" within notches 40 and 42 at points of intersection 39, thereby locking the stent 30 more reliably into the deployed configuration and resisting pressure exerted by the vessel to return to a smaller diameter.

Although not limited thereto, endoprosthesis 30 could be fabricated overall from or coated with one or curable materials, or comprise one or more curable materials at points of intersection 39, or within the interior of the woven fiber or fibers. Ultraviolet light is delivered within a device and points of intersection are "welded" together in the expanded and locked position. Following curing of such curable materials, the stability of the "nesting" function of notches 40 and 42 may be enhanced. In yet another alternative embodiment, endoprosthesis 30 could be fabricated from one or more curable materials and cured in a pattern utilizing photolithographic technique as discussed above, to enhance curing at notches 40 and 42. Further, endoprosthesis 30 could alternatively be processed to comprise a therapeutic incorporated into the materials comprising endoprothesis 30 or coated on its surface utilizing any of the technologies discussed above.

Figure 9:
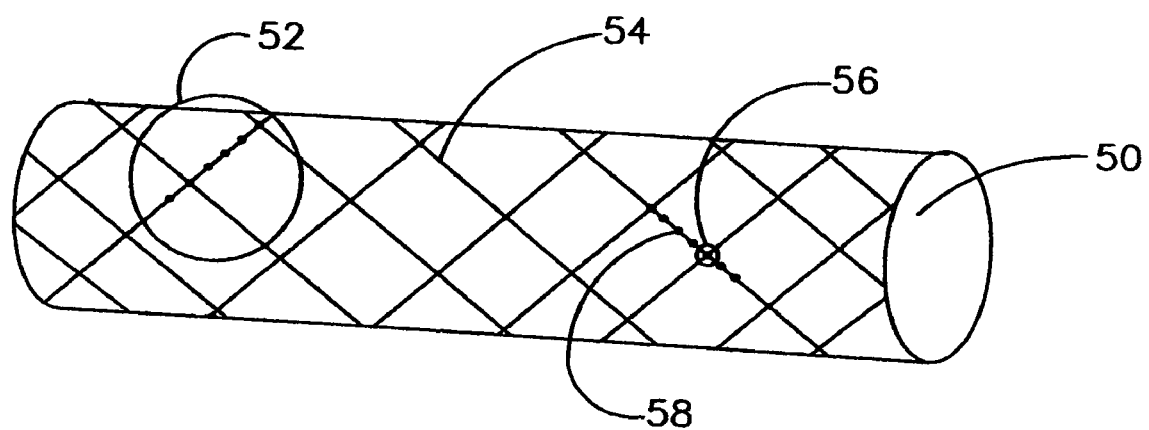
FIG. 9 depicts another embodiment according to the invention in its deployed configuration.
Figure 10:
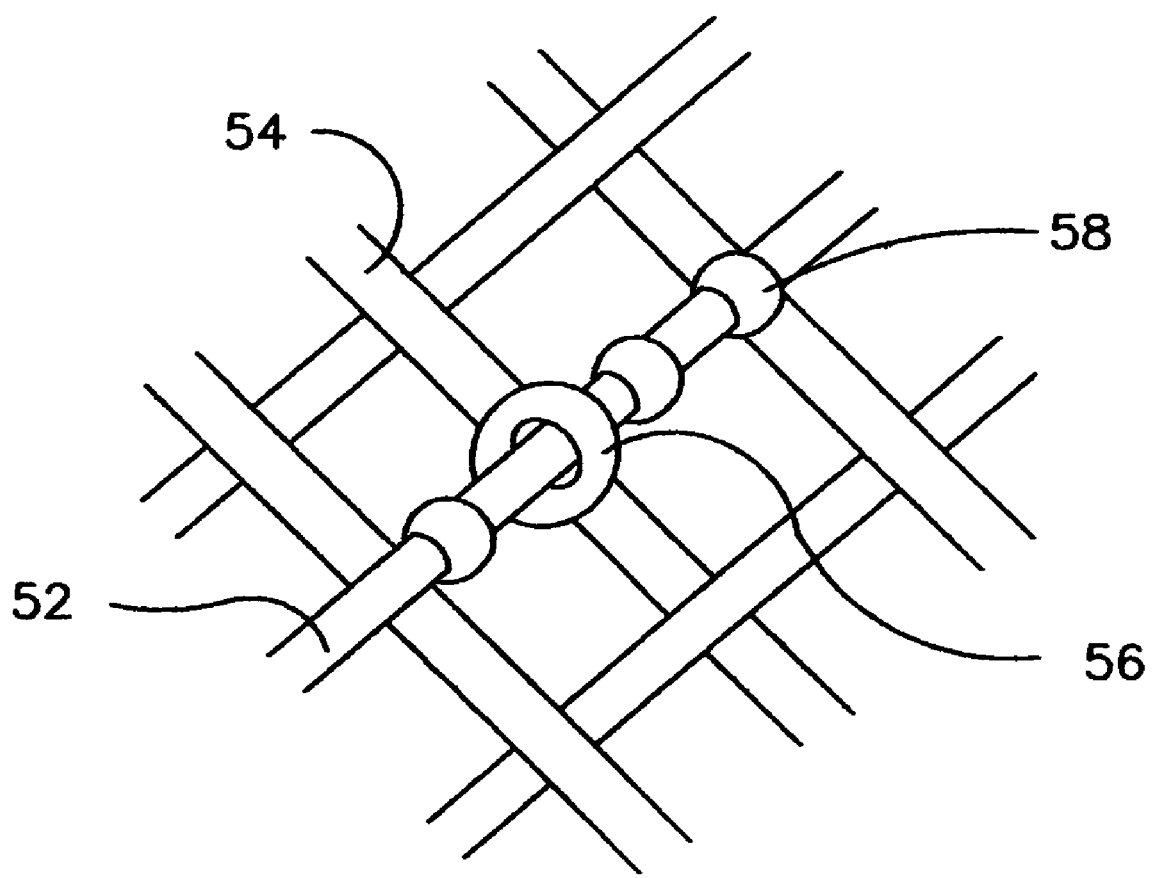
FIG. 10 shows detail area C of FIG. 9.

Yet another embodiment according to the invention can be more clearly described in relation to FIGS. 9 and 10. Similar to embodiments according to the invention discussed in relation to FIGS. 1–8, endoprosthesis 50, shown in FIG. 9 in its deployed configuration, also has a low-profile delivery configuration. Endoprosthesis 50 may be self-expanding, balloon-expandable, or balloon-assisted. Endoprosthesis 50 comprises fibers 52 and 54, which may be fabricated in any of the number of possible manners and from any of the number of possible materials as the fibers discussed above, are woven at angles to one another to form a generally tubular structure. Fibers 52 comprise bead-like "male" elements 58 and fibers 54 comprise "female" elements 56, which are configured to allow male elements 58 to pass through in one direction only. Upon expansion of stent 50 by appropriate means, male elements 58 pass through female elements 56, and cannot pass back through in the reverse direction. Fibers 52 are thereby "locked" in relation to one another, and endoprosthesis 50 is consequently "locked" in its deployed configuration once expanded to its desired diameter. Female elements 56 and male elements 58 may alternatively comprise curable materials and/or endoprosthesis 50 may be cured in a pattern to enhance the stability of stent 50 following deployment.

Figure 11A:
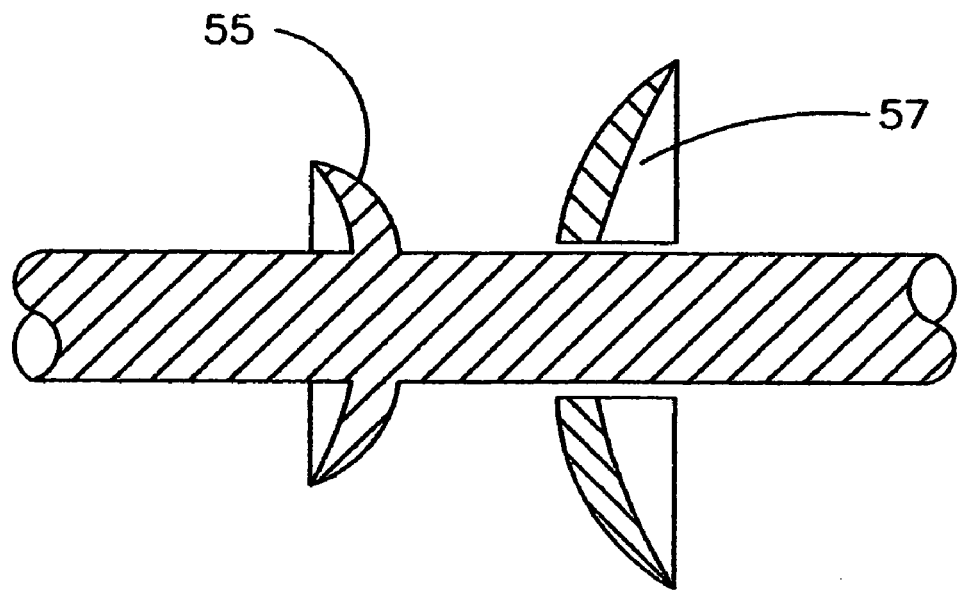
FIGS. 11A and 11B illustrate a component of an alternative embodiment according to the invention.
Figure 11B:
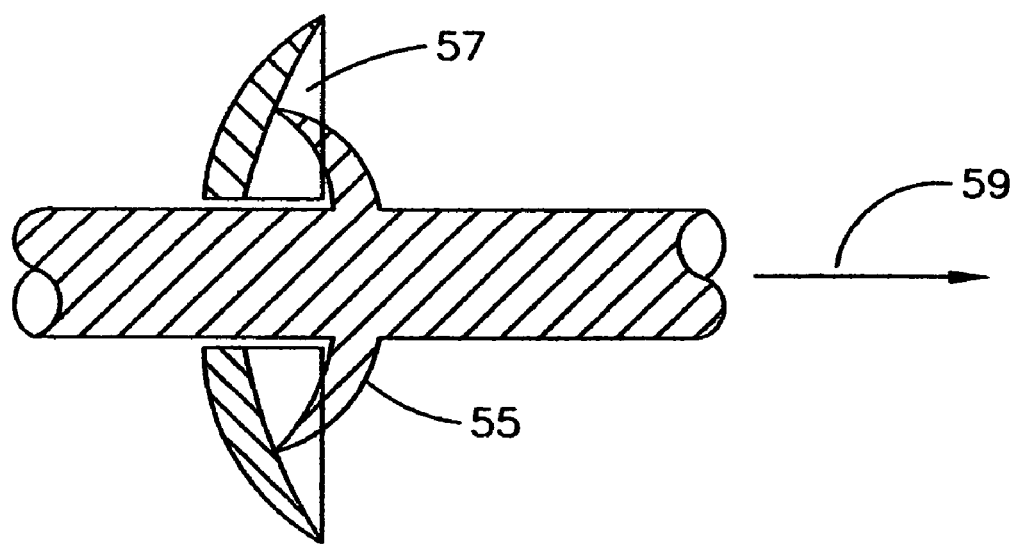

In FIGS. 11A and 11B, an alternative configuration of the invention as set forth in FIGS. 9–10 is illustrated. In FIG. 11A, male element 55 and female element 57 are illustrated prior to mating. Male element 55 is configured as a barb-like structure, and female element 57 is configured as a cup-like structure. In FIG. 11B, male element 55 has moved in direction of arrow 59, and has been irreversibly received within female element 57. Male element 55 cannot be pulled back through female element 57 in the direction opposite that represented by arrow 59. It should be emphasized, however, that the foregoing are merely examples, and that male and female elements may be configured in any of a number of suitable configurations for irreversible coupling.

Figure 12A:
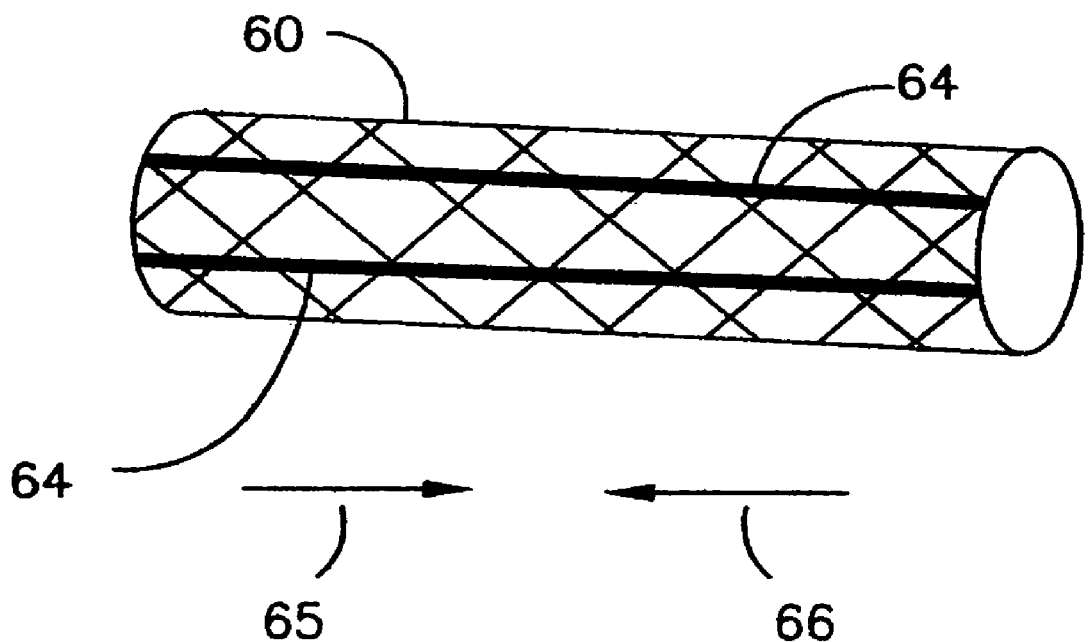
FIG. 12A is a plan view of yet another embodiment according to the invention in its deployed configuration.
Figure 12B:
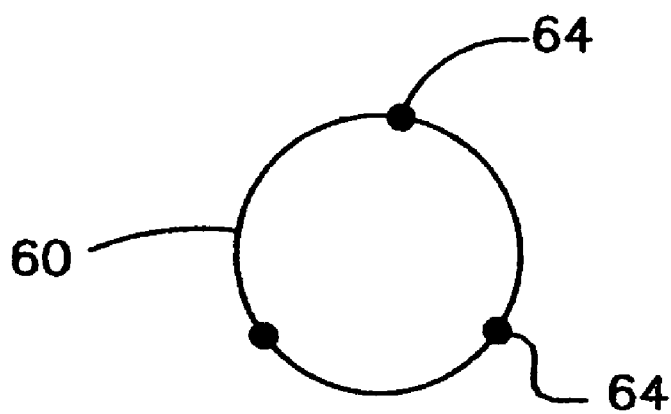
FIG. 12B shows an end view of the embodiment illustrated in FIG. 12A.

Turning now to an altogether alternative embodiment, endoprosthesis 60 is shown in FIG. 12. endoprosthesis 60 comprises a braided fiber structure similar to the embodiments illustrated above. Endoprosthesis 60 further comprises one or more axial members 64, which extend substantially the length of endoprosthesis 60. In the embodiment of FIG. 12A, endoprosthesis 60 comprises three axial members 64, spaced approximately 120 degrees from one another. Axial member 64 may be fabricated from any number of elastomeric or shape memory materials. Axial member 64 may be affixed to endoprosthesis 60 in any suitable manner known in the art including but not limited to the use of a suitable adhesive, chemically attached, melt bonded, or curable in situ, etc. FIG. 12B depicts an end view of the embodiment of FIG. 12. An example of the possible spacing of axial members 64 can be seen.

Axial members 64 exert a foreshortening force on endoprosthesis 60 in the direction of arrows 65 and 66. Such foreshortening force acts to prevent endoprosthesis 60 from elongating, thereby preventing a decrease in the diameter of endoprosthesis 60. Axial members 64 thereby act to "lock" endoprosthesis 60 at the desired deployed diameter. Although not limited thereto, axial members 64 and/or endoprosthesis 60, when in a reduced profile configuration, may be coated with a hydrophilic polymer in order to maintain endoprosthesis 60 in the reduced profile configuration. Upon exposure to physiological fluids, such hydrophilic polymer would erode, allowing axial member 64, and consequently endoprosthesis 60, to return to a larger profile, deployment diameter.

Figure 13A:
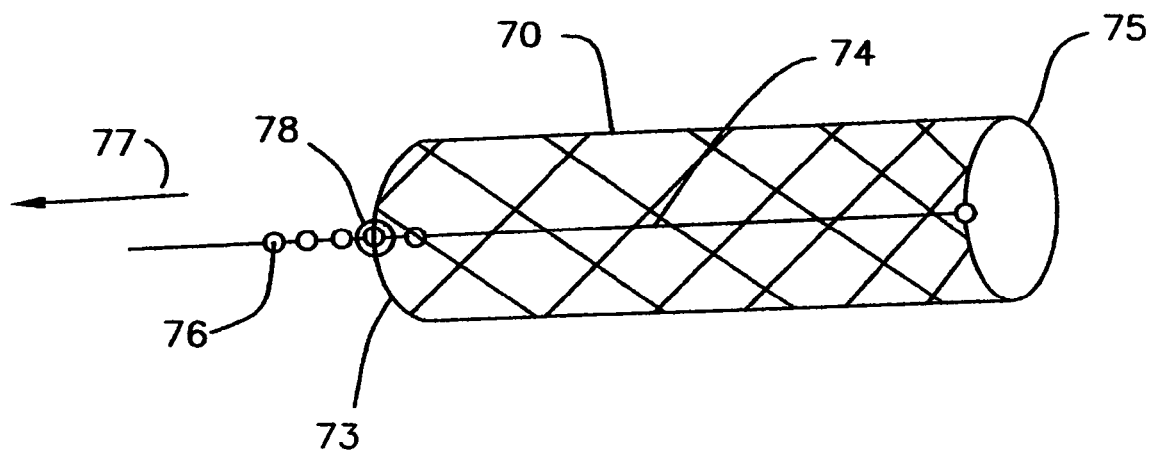
FIG. 13A is a plan view of an alternative embodiment according to the invention.
Figure 13B:
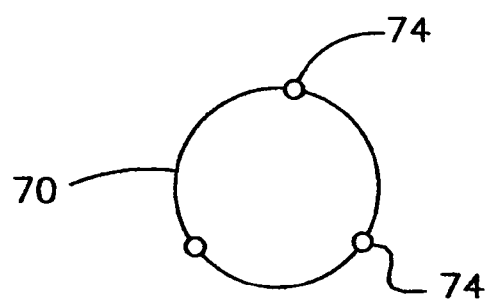
FIG. 13B is an end view of the embodiment of FIG. 13A.

FIG. 13A illustrates an embodiment similar to that discussed in relation to FIGS. 12A and 12B. In FIG. 13A, endoprosthesis 70 is shown in its deployed configuration. Endoprosthesis 70 comprises one or more axial element 74 affixed by any suitable means at or near distal terminus 75 of stent 70. Axial element 74 further comprises male elements 76 and female element 78 at or near proximal terminus 73 of stent 70. Upon deployment of endoprosthesis 70, axial element 74 is "tightened" to exert a foreshortening force upon endoprosthesis 70. Male elements 76, which can be of any number of suitable configurations, are pulled irreversibly through female element 74 in direction of arrow 77. Male elements 76 cannot pass in the opposite direction. Similar to the foregoing embodiments discussed, endoprosthesis 70 and axial element 74 may be fabricated using any of the aforementioned materials according to any of the aforementioned processes. FIG. 13B shows an end view of the embodiment discussed in relation to FIG. 13A.

Figure 14A:
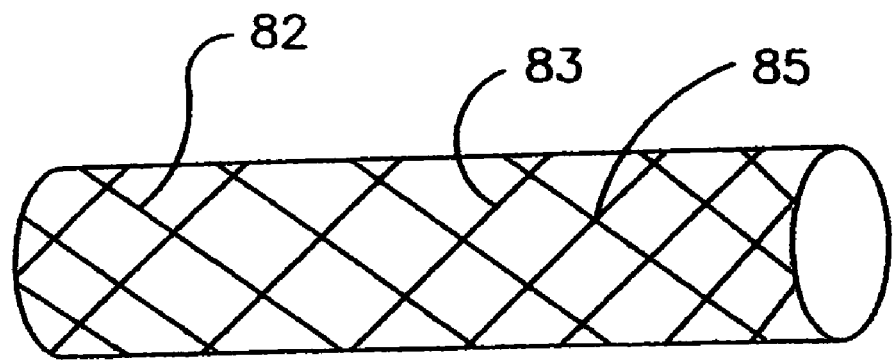
FIGS. 14A–14B illustrate a plan view of an embodiment according to the invention.
Figure 14B:
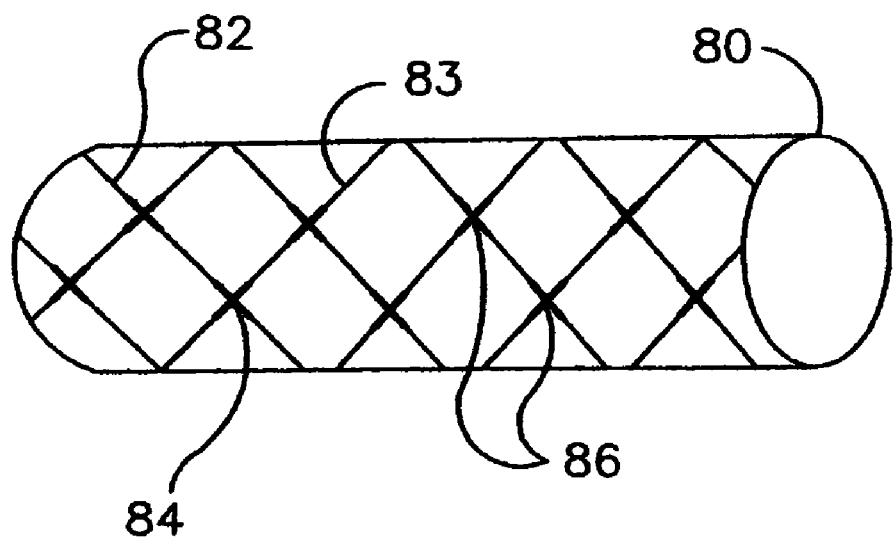

FIGS. 14A and 14B illustrate an alternative embodiment according to the invention. Endoprosthesis 80 is similar to the embodiments described in relation to FIGS. 1–13 to the extent that it comprises a braided, generally tubular structure fabricated from two or more of any number of suitable materials. Further, following deployment, endoprosthesis 80 comprises one or more locking regions 86 at one or more fiber points of intersection 84. Locking regions 86 may alternatively be defined by numerous other configurations. In the embodiment of FIG. 14A–B, locking regions 86 comprise a chemical bond between fibers 82 and 83.

More specifically, endoprosthesis 80 comprises alginate fibers 82 and calcium fibers 83. Calcium fibers 83 are coated with one or more of any number of suitable hydrophilic coatings 85. Upon deployment of endoprosthesis 80 within an aqueous environment, hydrophilic coating 85 dissolves, leaving calcium fibers 83 exposed and in contact with alginate fibers 82 at one or more, and typically numerous, fiber points of intersection 84. Upon contact between alginate fibers 82 with calcium fibers 83, a chemical reaction between the materials produces a material that cures at body temperature. Locking regions 86 are thereby formed, as shown in FIG. 14B. Endoprosthesis 80 could alternatively be fabricated from materials curable by other means, including photocurable materials, and potentially cured according to a desired pattern using photolithographic technique as set forth in more detail above.

Figure 14C:
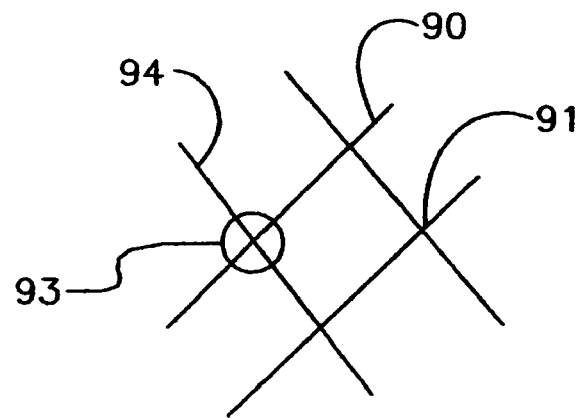
FIGS. 14C–14E illustrate alternative embodiments of the locking regions of endoprostheses according to the invention.
Figure 14D:
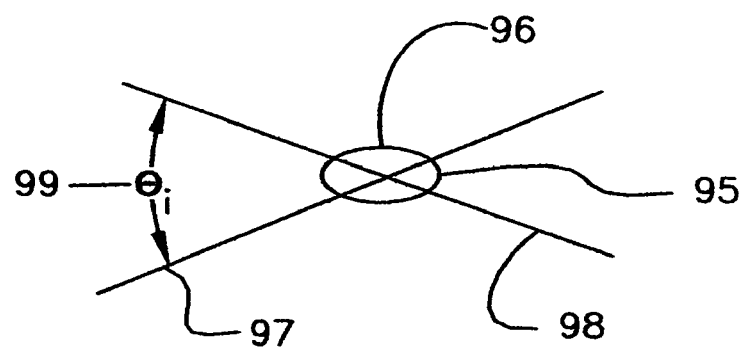
Figure 14E:
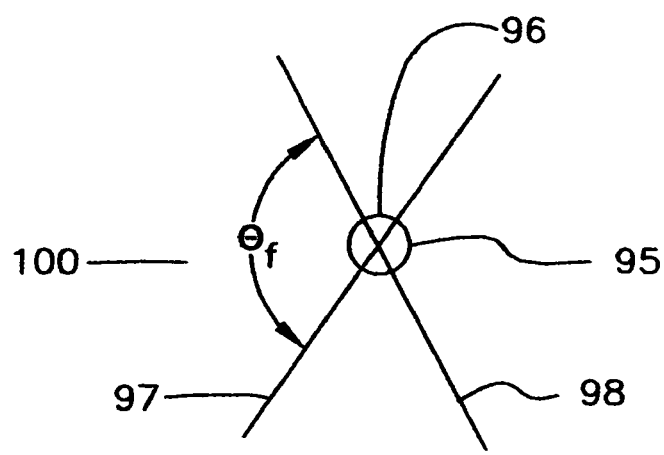

FIGS. 14C–E represent different embodiments according to the invention that also comprise one or more locking regions at or near fiber crossing points. In the embodiment of FIG. 14C, one or more fiber crossing points 91 comprise thermocouple 93 composed of any suitable material. Once an endoprosthesis comprising thermocouple 93 achieves its deployed configuration, inductive heating may be employed to join fibers 90 and 94 at points of intersection 91, thereby locking such an endoprosthesis in its deployed configuration. Alternatively, a radiofrequency signal may be employed to heat thermocouple 93 in order to weld or otherwise join fibers at or near points of intersection.

FIG. 14D–E illustrate an alternative embodiment of a locking region of an endoprosthesis before and after deployment. In FIG. 14D, prior to deployment, fiber 97 crosses fiber 98 at angle 99. Locking element 95 is disposed at or near point of intersection 96. Following deployment by self expansion or other means, fiber 97 then crosses fiber 98 at angle 100, causing locking element 95 to engage, thereby locking fibers 97 and 98 at or near angle 100, and consequently an endoprosthesis comprising locking element 95 to remain in the deployed configuration.

Figure 15:
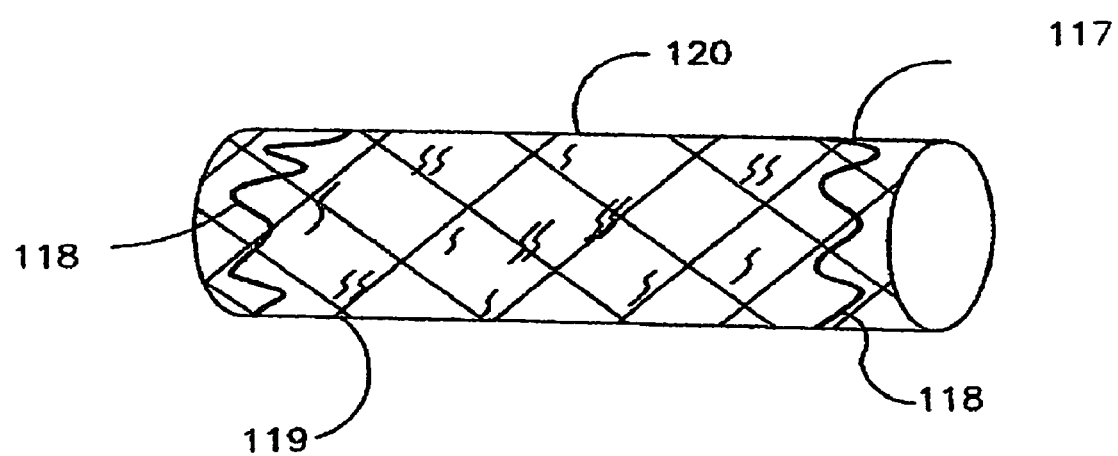
FIG. 15 is a plan view of yet another embodiment according to the invention in its expanded configuration.

Any of the foregoing embodiments may further comprise a therapeutic agent to be eluted independently or as the endoprosthesis erodes. As a first step in preparing any of the foregoing endoprostheses, a suitable polymer in supercritical carbon dioxide solution may be admixed with a hydrophobic therapeutic agent. As a result, the hydrophobic therapeutic agent is incorporated into the polymer. Alternatively, an embodiment according to the invention may comprise an outer layer 120, shown in FIG. 15, into which a hydrophilic therapeutic agent has been incorporated. As described above, following fabrication, endoprosthesis 117, formed from any of the aforementioned materials, has been immersed in a solution of polymer, water and hydrophilic therapeutic agent, underlying a "blanket" of supercritical carbon dioxide. The carbon dioxide renders the polymer more receptive to the incorporation of therapeutic agent. The polymer comprising the therapeutic agent forms layer 120 on the surface of endoprosthesis 117.

Endoprosthesis 117 further comprises end cap 118, formed of a shape memory material, and disposed at or near one or more ends 119. End cap 118 exerts an outward radial force serves to maintain endoprosthesis 117 in its deployed configuration.

While particular forms of the invention have been illustrated and described above, the foregoing descriptions are intended as examples, and to one skilled in the art will it will be apparent that various modifications can be made without departing from the spirit and scope of the invention.

We claim:

1. An endoprosthesis comprising a length, one or more fibers and an axis extending generally along said length, said one or more fibers comprising a braid comprising one or more points of intersection, said endoprosthesis further defining a generally tubular structure, a delivery configuration and a deployed configuration, said one or more fibers comprising one or more locking elements proximate said one or more said one or more points of intersection, wherein upon deployment, one or more of said fibers engages itself or another fiber proximate one or more of said points of intersection via said locking elements to maintain said endoprosthesis in said deployed configuration, and where said endoprosthesis does not comprise a primarily axially oriented element or fiber.

2. The endoprosthesis according to claim 1 wherein said endoprosthesis comprises one or more erodible materials.

3. The endoprosthesis of claim 1 wherein said one or more locking elements comprise locking protrusions.

4. The endoprosthesis of claim 1 wherein said one or more locking elements comprise one or more notches.

5. The endoprosthesis of claim 1 wherein said one or more locking elements comprise male and female elements.

6. The endoprosthesis of claim 1 wherein said one or more fibers comprises a chemical bond at said one or more points of intersection when said endoprosthesis is in said deployed configuration.

7. The endoprosthesis of claim 1 wherein said one or more locking elements comprise one or more thermocoupling element.

8. The endoprosthesis of claim 1 wherein said one or more fibers comprises one or more curable materials.

9. An endoprosthesis comprising a length, one or more fibers, an axis extending generally along said length, said one or more fibers oriented substantially in a first direction and in a second direction to form one or more points of intersection and a woven tubular structure also comprising a delivery configuration and a deployed configuration, said one or more fibers comprising one or more locking elements proximate said one or more points of intersection, wherein upon deployment, one or more of said fibers engages itself or another fiber proximate one or more said points of intersection via said locking elements to maintain said endoprosthesis in said deployed configuration, and where said endoprosthesis does not comprise a fiber oriented in substantially a third direction.

10. The endoprosthesis according to claim 1 wherein one or more of said fibers is hollow and filled with a curable material.

11. The endoprosthesis according to claim 1 wherein one or more of said fibers is hollow and comprises polymers chains in substantially circumferential orientation.

* * * * *